(12) United States Patent
Nishida et al.

(10) Patent No.: US 7,981,653 B2
(45) Date of Patent: Jul. 19, 2011

(54) HIGHLY EFFICIENT HYPERTHERMOPHILIC DNA LIGASE

(75) Inventors: Hirokazu Nishida, Kokubunji (JP); Maiko Tanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 505 days.

(21) Appl. No.: 12/028,372

(22) Filed: Feb. 8, 2008

(65) Prior Publication Data

US 2009/0061481 A1    Mar. 5, 2009

(30) Foreign Application Priority Data

Mar. 30, 2007 (JP) ................................ 2007-093436

(51) Int. Cl.
*C12N 9/10* (2006.01)
*C12N 9/00* (2006.01)
(52) U.S. Cl. .................... 435/193; 435/183; 530/350
(58) Field of Classification Search .................. None
See application file for complete search history.

(56) References Cited

U.S. PATENT DOCUMENTS 6,576,453 B2 * 6/2003 Barany et al. ............... 435/193

OTHER PUBLICATIONS

Ngo et al., The Protein Folding Problem and Tertiary Structure Prediction, 1994, Merz et al. (ed.), Birkhauser, Boston, MA, pp. 433 and 492-495.*
Nishida et al., Journal of Molecular Biology, vol. 360, No. 5, pp. 956-967, Jul. 2006.*
Ishikawa, Kazuhiko, "Development of the World's Most Thermostable Enzyme (DNA Ligase) for Gene Diagnosis", National Institute of Advanced Industrial Science and Technology, Sep. 10, 2003, 4 pages.

* cited by examiner

*Primary Examiner* — Richard G Hutson
(74) *Attorney, Agent, or Firm* — Mattingly & Malur, PC

(57) ABSTRACT

Disclosed is a modified hyperthermophilic DNA ligase having improved DNA binding ability and reactivity. The modified hyperthermophilic DNA ligase has an amino acid sequence corresponding to the amino acid sequence of a heat-resistant DNA ligase derived from a thermophilic bacterium, a hyperthermophilic bacterium, a thermophilic archaebacterium, or a hyperthermophilic archaebacterium, except with at least two of the charged amino acids in the C-terminal helix region each being substituted by alanine, threonine, or serine residues.

5 Claims, 2 Drawing Sheets

FIG. 2

```
                                                                Motif VI
Archaea   (Crenarchaeota)
Pae  502  HRHPRVVSK--MEADVWFVPQVVIEVIGAEITLSPLHTCCLGAVRPGVGLAVRFPRFTGRYRSDKSPEQATTVAEMLELYKRQKKVVQPE------ 589
Dam  509  TPHPRVVST--MVPDVWLTPALVAEIIGAEITISPLHTCCKDQYAEGG-LSIRFPRFIR-WRPDKSPEDATTNREILEMYKSQLKKIEEKPSDQSV---- 600

Archaea   (Euryarchaeota)
Afu  488  QQGK-----------KVEFIPKYVFEVAYQEIQKSPKYESG--------YALRFPRFVR-LPDDKDVDEADTIERV-ENLYKLQFEVKRQ--------- 556
Mth  493  RKGR-----------KLLVRPEIILEVAYSEIVKSPEYESG--------YSLRFPVVKR-IRDDLCLDDVDTVGRI-ESLFQSGQPDQPG--------- 561
Mja  507  DLGE-----------EVEVEPKIVIEVAYEEIQKSDKYPCG--------YALRFPRVVR-FRFDKGVNEINTIEDV-ERIYEIQRGR-K---------- 573
Tko  493  QEGK-----------FVEIEPKFVIEVTYQEIQKSPKYKSG--------FALRFPRYVA-LREDKSPEEADTIERVAELYELQERFKAKK--------- 562
Pab  490  EEGK-----------RVWIQPKVVIEVTYQEIQKSPKYRSG--------FALRFPRYVA-LREDKGPEDADTIERIAQLYELQERMKGKV--------- 559
Pfu  490  EEGK-----------RVWLQPKVVIEVTYQEIQKSPKYRSG--------FALRFPRFVA-LRDDKGPEDADTIERIAQLYELQEKMKGKVES------- 561

Eukarya
hul  819  SPRPYVRIDGAVIPOHWLDPSAVWEVKCADLSLSPIYPAARGLVDSDKGISLRFPRFIR-VREDKQPEQATTSAQVACLYRKQSQIQNQQGEDSGSDPEDTY 919
Scl  671  GPKATFVFDSSAEPDVWFEPTTLFEVLTADLSLSPIYKAGSATFDKG--VSLRFPRFLR-IREDKGVEDATSSDQIVELYENQSHMQN------------ 755

Pae, Pyrobaculm aerophilum     (U82370)
Dam, Desufurolobus ambivalens  (Q02093)
Afu, Archaeglobus fulgidus     (O29632)
Mth, Methanobacterium thermoautotrophicum  (U51624-4)
Mja, Methanococcus jannaschii  (U67474-4)
Tko, Thermococcus kodakaraensis  (AB042527)
Pab, Pyrococcus abyssi         (B75173)
Pfu, Pyrococcus furiosus       (NC003413 – complete genome – )
hul, Homo sapiens
Scl, Saccharomyces cerevisiae  (Z74212-1)
```

US 7,981,653 B2

HIGHLY EFFICIENT HYPERTHERMOPHILIC DNA LIGASE

CLAIM OF PRIORITY

The present application claims priority from Japanese application JP 2007-093436 filed on Mar. 30, 2007, the content of which is hereby incorporated by reference into this application.

FIELD OF THE INVENTION

The present invention relates to highly-efficient hyperthermophilic DNA ligases. Specifically, it relates to a highly-efficient hyperthermophilic DNA ligase obtained by substituting at least two of charged amino acids in a carboxyl-terminal (C-terminal) helix region of a DNA ligase; and to a highly-efficient hyperthermophilic DNA ligase which has deletions in the C-terminal helix region, in addition to the substitutions.

BACKGROUND OF THE INVENTION

DNA ligase is an enzyme having the activity of linking DNA chains by forming a phosphodiester bond between a 3'-hydroxy group and 5'-phosphoryl group of DNA and is involved in DNA replication and repair of damaged DNA strands in vivo. DNA ligase is also used in a recently developed gene amplification technique known as a ligase chain reaction (LCR). LCR is a technique by which a target gene is amplified or detected through a temperature-cycling reaction using a heat-resistant DNA ligase. For more efficiently carrying out LCR, heat-resistant ligases with higher activities have been searched and commercially supplied.

DNA ligases derived from hyperthermophilic archaeon and having excellent thermal stability have been recently found (National Institute of Advanced Industrial Science and Technology (AIST) of Japan, On-line Press Release (2003): http://www.aist.go.jp/aist_j/press_release/pr2003/pr20030910/pr20030910.html; "Development of Extremely Heat-resistant DNA Ligase for Genetic Diagnosis"; corresponding to JP-A NO. 2004-248636 and US-A No. 20040259123). These heat-resistant DNA ligases excel in thermostability but have a disadvantage of poor reactivity, because they have a very poor binding ability to DNA. In contrast, phage-derived DNA ligases are known as DNA ligases having high binding ability to DNA (hereinafter briefly referred to as "DNA binding ability"). These DNA ligases are, however, poor in thermal resistance and thereby not suitable for LCR. Thus, no DNA ligase that has high thermal resistance and high DNA binding ability and makes it possible to carry out LCR at a sufficient turnover has yet been found.

SUMMARY OF THE INVENTION

An object of the present invention is to provide a DNA ligase with high activity which as high thermal resistance and high DNA binding ability and can react with a substrate at a sufficient turnover.

After intensive investigations, the present inventors found that the C-terminal helix region of a DNA ligase controls or reduces the flexibility of the DNA ligase and thereby reduces DNA binding ability. They succeeded to improve the DNA binding ability of a DNA ligase by deleting part or all of the C-terminal helix region. The resulting DNA ligase, however, still had a disadvantage of poor stability, although it had improved DNA binding ability. This was probably because hydrophobic amino acids in the vicinity of C-terminal helix region are exposed from the surface of the protein (DNA ligase) as a result of the deletion of the C-terminal helix region, whereby the DNA ligase has lowered hydrophilicity. The present inventors made further investigations to solve this and have found that a DNA ligase with extremely high activity can be obtained by substituting part or all of charged amino acids in the C-terminal helix region by an amino acid which is hydrophilic and has a small side chain (alanine, threonine, and/or serine). They have also found that a DNA ligase having improved activities not only at high temperatures but also at around 20° C. to 30° C. can be obtained by employing the substitutions of the charged amino acids in combination with the deletions of the C-terminal helix region. The present invention has been made based on these findings.

Specifically, the present invention relates to a modified hyperthermophilic DNA ligase corresponding to a heat-resistant DNA ligase derived from one selected from the group consisting of a thermophilic bacterium, a hyperthermophilic bacterium, a thermophilic archaebacterium, and a hyperthermophilic archaebacterium, except with at least two of charged amino acids in a C-terminal helix region thereof being substituted by alanine, threonine, or serine. The charged amino acids to be substituted are preferably amino acids exposed from the surface of protein. Examples thereof include four amino acids, in which, when the amino acid sequence of the heat-resistant DNA ligase is aligned with the amino acid sequence of a heat-resistant DNA ligase derived from Pyrococcus furiosus represented by SEQ ID NO: 1, the four amino acids correspond to the aspartic acid residue at position 540, the glutamine residue at position 547, the lysine residue at position 554, and the lysine residue at position 558 of the amino acid sequence of SEQ ID NO: 1.

Amino acids to substitute may be amino acids which are hydrophilic and have small side chains, such as alanine, threonine, and serine. They preferably substitute at least two of the four amino acids. In a preferred embodiment, at least two of the four amino acids are substituted by alanine.

In another preferred embodiment, the amino acid sequence of the modified hyperthermophilic DNA ligase further includes deletions of four or more and twelve or less amino acid residues from the C terminus in the C-terminal helix region, in addition to the substitutions.

A preferred example of the heat-resistant DNA ligase includes a heat-resistant DNA ligase derived from *Pyrococcus furiosus*.

According to other aspects of the present invention, there are provided a DNA encoding the modified hyperthermophilic DNA ligase, and an expression vector containing the DNA.

According to yet another aspect of the present invention, there is provided a method of preparing a modified hyperthermophilic DNA ligase. This method includes the steps of cultivating a host cell bearing the expression vector introduced thereinto to yield a harvest, and recovering a protein having a DNA ligase activity from the harvest.

According to other aspects of the present invention, there are provided a method of carrying out a ligase chain reaction (LCR) using the modified hyperthermophilic DNA ligase according to the present invention, and a kit for use in the method.

According to the present invention, there are provided modified hyperthermophilic DNA ligases which are superior in DNA binding ability and reactivity (stability) to native one. The modified hyperthermophilic DNA ligases according to the present invention realize a method of carrying out a ligase chain reaction (LCR) which can be conducted at a high rate with high specificity, whereby enables efficient gene amplifications and detection of single nucleotide polymorphism (SNP). Using the modified hyperthermophilic DNA ligases according to the present invention, genetic engineering can be conducted with high selectivity.

BRIEF DESCRIPTION OF THE DRAWINGS

FIG. 2 shows alignments of different DNA ligases (SEQ ID Nos 26-35, respectively, in order of appearance).

DETAILED DESCRIPTION OF THE PREFERRED EMBODIMENTS

1. Modified Hyperthermophilic DNA Ligase

Figure 1:
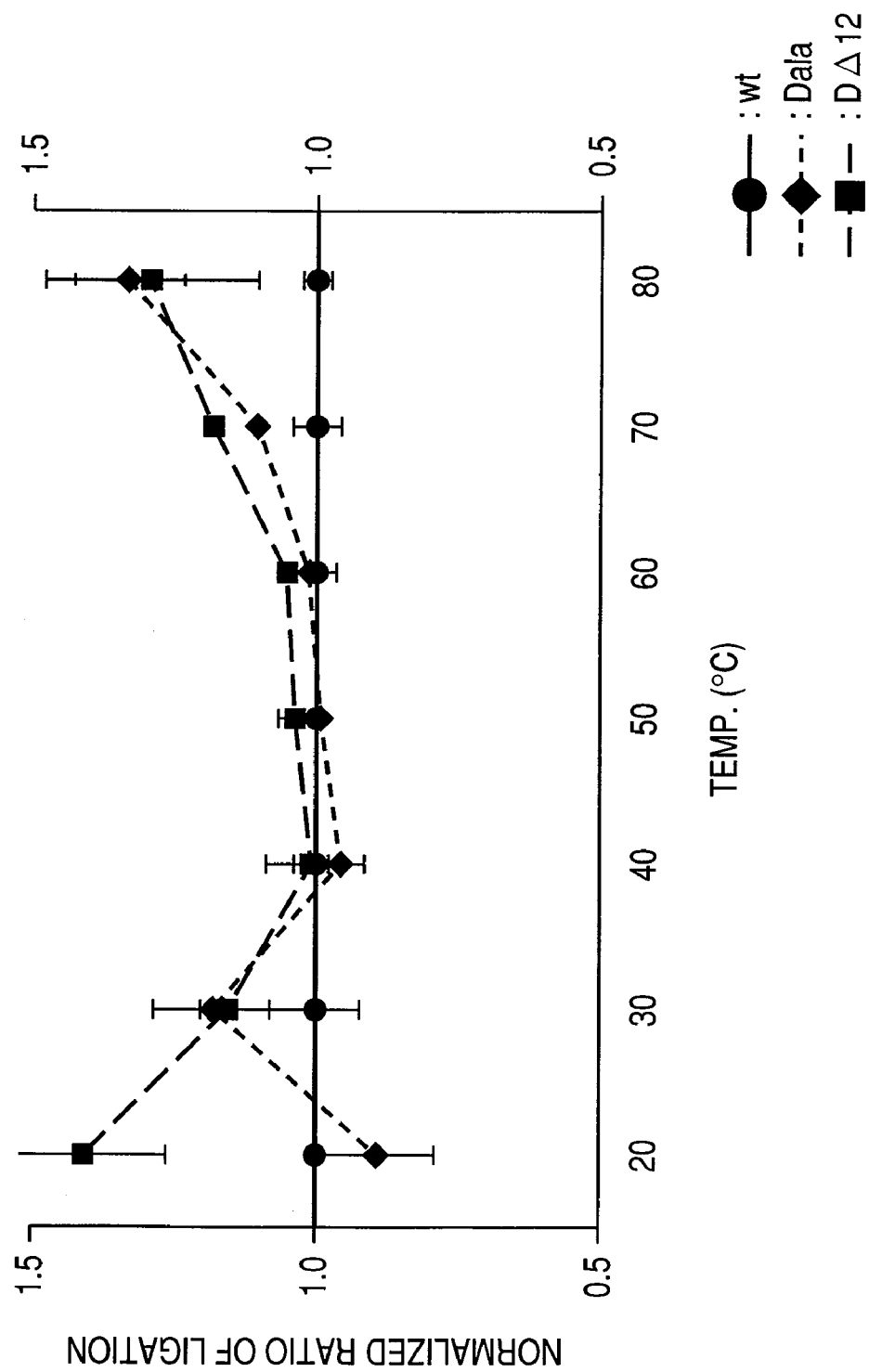
FIG. 1 is a graph showing specific activities of C-terminal helix-modified ligases (Dala, DΔ12) at varying temperatures with the reactivity of a wild-type ligase being 1.

The present invention relates to modified hyperthermophilic DNA ligases which are superior in DNA binding ability and reactivity (stability) to wild-type (native) one. The modified hyperthermophilic DNA ligases are prepared by substituting at least two of charged amino acids each by alanine, threonine, or serine, in which the charged amino acids are present in the C-terminal helix region of a heat-resistant DNA ligase derived from a thermophilic bacterium, a hyperthermophilic bacterium, a thermophilic archaebacterium, or a hyperthermophilic archaebacterium.

The "heat-resistant DNA ligase" for use in the present invention is a DNA ligase which excels in thermal stability and is derived from one selected from thermophilic bacteria such as *Bacillus stearothermophilus*; hyperthermophilic bacteria such as *Thermotoga maritima*; thermophilic archaebacteria such as *Thermoplasma volcanium*; and hyperthermophilic archaeon such as *Aeropyrum pernix*. The amino acid sequences of such heat-resistant DNA ligases are already known and registered, for example, in public database GenBank: *Archaeglobus fulgidus* (029632), *Methanobacterium thermoautotrophicum* (U51624-4), *Methanococcus jannaschii* (U67474-4), *Thermococcus kodakaraensis* (AB042527), *Pyrococcus abyssi* (B75173), and *Pyrococcus furiosus* (NC003413—complete genome—). The heat-resistant DNA ligase for use in the present invention is preferably one derived from a hyperthermophilic bacterium or a hyperthermophilic archaebacterium. In a typically preferred embodiment, the heat-resistant DNA ligase is a DNA ligase derived from *Pyrococcus furiosus* (SEQ ID NO: 1).

Regular DNA ligases act at 20° C. to 30° C., whereas DNA ligases derived from these bacteria can maintain their activities stably at high temperatures and are thereby very useful in LCR and other nucleotide amplification techniques and genetic engineering techniques requiring temperature-cycling reactions. Although not specifically limited, the heat-resistant DNA ligase for use in the present invention is preferably one that can maintain its enzymatic activity at temperatures of preferably 70° C. or more, and more preferably 90° C. or more.

The heat-resistant DNA ligase for use in the present invention has a helix region at the C terminus and has a homology with the DNA ligase derived from *Pyrococcus furiosus* (SEQ ID NO: 1). The heat-resistant DNA ligase may have an amino acid sequence identity of, for example, 60% or more, preferably 70% or more, and more preferably 80% or more, with the amino acid sequence of SEQ ID NO: 1. The term "helix region" used herein refers to a region of successive amino acids constituting a helix of DNA ligase. Most of DNA ligases such as those derived from humans, yeasts, and bacteria have a helix region at the C terminus. The C-terminal helix region is believed to reinforce the structure of DNA ligase but, on the other hand, reduces the flexibility of DNA ligase. This reduces the DNA binding ability and causes lowered reactivity.

According to the present invention, at least two of charged amino acids, such as glutamic acid, aspartic acid, lysine, arginine, and histidine, present in the C-terminal helix region are each substituted by an amino acid which is hydrophilic and has a small side chain (alanine, threonine, or serine).

More specifically, at least two selected from four amino acids are substituted in the above manner, in which, when the amino acid sequence of the subject heat-resistant DNA ligase is aligned with the amino acid sequence of a heat-resistant DNA ligase derived from *Pyrococcus furiosus* represented by SEQ ID NO: 1, the four amino acids correspond to the aspartic acid residue at position 540, the glutamine residue at position 547, the lysine residue at position 554, and the lysine residue at position 558 of the amino acid sequence of SEQ ID NO: 1. FIG. 2 shows alignments by way of example. Motif VI in FIG. 2 is one of six regions (Motifs I to VI) which are commonly found in all DNA ligases and have high homologies. When a region to be modified is in the vicinity of the motif, the region can be easily found to be homologous in alignment. The C-terminal helix region to be modified herein is in the very vicinity of Motif VI.

Initially, the present inventors succeeded to yield a DNA ligase having improved flexibility and accordingly improved DNA binding ability by deleting four or more and twelve or less amino acid residues from the C terminus in the C-terminal helix region. However, they found that the deletion causes exposure of hydrophobic amino acids and thereby lowers the stability of DNA ligase. To avoid this, they substituted part or all of charged amino acids in the C-terminal helix region in the above manner and found that the resulting DNA ligase has a high reactivity at high temperatures even when it has no deletion in the C terminus. They further found that a DNA ligase having high reactivity not only at high temperatures but also at 20° C. to 30° C. can be obtained by employing the deletion of the C-terminal helix region in combination with the substitution.

The amino acid substitution is carried out on at least two of charged amino acids. This is because mutations of at least two amino acid residues may be required for effectively reducing interdomain interactions.

As is described above, the amino acid substitution can be carried out in combination with the deletion of the C-terminal helix region. The deletion of the C-terminal helix region is preferably carried out by deleting successive four or more and twelve or less amino acids from the C terminus of the DNA ligase.

The amino acid substitution and the deletion in the C terminus region can be carried out according to processes known to those skilled in the art. The amino acid substitution can be carried out, for example, substituting an amino acid codon to be modified by a target amino acid codon through site-directed mutagenesis. The deletion of C terminus can be carried out by inserting a stop codon to thereby delete a C-terminal amino acid sequence downstream from the stop codon.

The resulting DNA ligase has high reactivity at high temperatures of 70° C. to 80° C. and is useful in nucleotide amplification techniques and genetic engineering techniques requiring temperature-cycling reactions.

2. Preparation of Modified Hyperthermophilic DNA Ligase Through Recombination

2.1 DNA Encoding Modified Hyperthermophilic DNA Ligase

A DNA encoding a modified hyperthermophilic DNA ligase according to an embodiment of the present invention is obtained by introducing site-directed mutagenesis or introducing site-directed mutagenesis in combination with a stop codon into a gene of a known native heat-resistant DNA ligase to thereby introduce C-terminal region deletion thereinto. The introduction of site-directed mutagenesis can be easily carried out using a commercially available kit such as the QuikChange XL Site-Directed Mutagenesis Kit (STRATAGENE) or the Transformer™ Site-Directed Mutagenesis Kit (CLONTECH).

2.2 Expression Vector

Next, an expression vector is prepared by ligating or inserting the DNA encoding the modified hyperthermophilic DNA ligase into a known vector such as a plasmid. The vector herein is not particularly limited, as long as it can replicate in a host, and examples thereof include a plasmid DNA and a phage DNA.

Examples of the plasmid DNA include plasmids derived from *Escherichia coli*, such as pBR322, pBR325, pUC18, pUC119, pTrcHis, pBlueBacHis, and pET21, of which pET21 plasmid having an intensive T7 promoter is preferred; plasmids derived from *Bacillus subtilis*, such as pUB110 and pTP5; and plasmids derived from yeasts, such as YEp13, YEp24, YCp50, and pYE52. Examples of the phage DNA include lambda phage.

The insertion of the gene DNA into the vector is carried out, for example, by a process of cleaving the DNA which has been purified with a suitable restriction enzyme and inserting a fragment into a suitable restriction enzyme site or multi-cloning site of the vector DNA to thereby ligate the DNA to the vector.

To allow a host to express such a foreign gene, a suitable promoter is arranged upstream of the structural gene. The promoter is not particularly limited and can be any one that is known to function in the host. Such promoters suitable for use in corresponding hosts will be described in detail in the aftermentioned transformants. Where necessary, there may be arranged, for example, a cis-element such as an enhancer, a splicing signal, a polyadenylation signal, a ribosome-binding sequence (Shine-Dalgarno sequence (SD sequence)), and/or a terminator sequence.

Examples of plasmids which make it possible to express the modified hyperthermophilic DNA ligase according to the present invention include pET21d-PfuLigDala and pET21d-PfuLigDΔ12 obtained according to the present invention.

2.3 Modified Hyperthermophilic DNA Ligase Expression System (Host Cell)

Next, the expression vector is introduced into a host so that the host can express the target gene. Thus, a modified hyperthermophilic DNA ligase expression system is prepared. The host for use herein is not particularly limited, as long as it can express the modified hyperthermophilic DNA ligase according to the present invention. Examples of the host include bacteria including those belonging to the genus *Escherichia*, such as *Escherichia coli*; the genus *Bacillus*, such as *Bacillus subtilis*; the genus *Pseudomonas*, such as *Pseudomonas putida*; and the genus *Rhizobium*, such as *Rhizobium meliloti*; yeasts such as *Saccharomyces cervisiae, Schizosaccharomyces pombe*, and *Pichia pastoris*; animal cells such as COS and CHO cells; and inset cells such as Sf19 and Sf21 cells.

When a bacterium such as *Escherichia coli* is used as a host, the expression vector (recombinant vector) according to the present invention is preferably autonomously replicable in the bacterium and includes a promoter, a ribosome-binding sequence, the gene according to the present invention, and a transcription termination sequence. The expression vector may further contain a gene for regulating the promoter. The *Escherichia coli* can be, for example, *Escherichia coli* strain HMS174 (DE3), K12, DH1, or B. The *Bacillus subtilis* can be, for example, *Bacillus subtilis* strain MI 114 or 207-21. The promoter is not particularly limited, as long as it can be expressed in a host such as *Escherichia coli*, and examples thereof include promoters derived from *Escherichia coli* or phages, such as trp promoter, lac promoter, $P_L$ promoter, and $P_R$ promoter. An artificially modified promoter such as tac promoter can also be used. The process of introducing the expression vector into the bacterium is not particularly limited and can be, for example, electroporation or a process of using calcium ion [Cohen, S. N. et al., *Proc. Natl. Acad. Sci. USA*, 69:2110-2114 (1972).

When a yeast such as *Saccharomyces cervisiae, Schizosaccharomyces pombe*, or *Pichia pastoris* is used as a host, the promoter is not particularly limited, as long as it can be expressed in the yeast. Examples of the promoter include gall promoter, gal10 promoter, heat-shock protein promoter, MFα1 promoter, PHO5 promoter, PGK promoter, GAP promoter, ADH promoter, and AOX1 promoter. The process of introducing the expression vector into the yeast is not particularly limited and can be, for example, electroporation [Becker, D. M. et al., *Methods. Enzymol.*, 194:182-187 (1990)], the spheroplast method [Hinnen, A. et al., *Proc. Natl. Acad. Sci., USA*, 75:1929-1933 (1978)], or the lithium acetate method [Itoh, H., *J. Bacteriol.*, 153:163-168 (1983)].

2.4 Cultivation of Transformant

The modified hyperthermophilic DNA ligase according to the present invention can be obtained by cultivating the transformant in a suitable medium, and collecting a protein having a DNA ligase activity from the culture. The process for cultivating the transformant according to the present invention is selected as appropriate according to the host. The culture medium for cultivating a transformant obtained from a microorganism such as *Escherichia coli* or yeast as a host may be either a natural or synthetic medium as long as it contains a carbon source, a nitrogen source, and inorganic salts which can be utilized by the microorganism and the transformant can efficiently be cultivated.

During the cultivation, an antibiotic such as ampicillin or tetracycline may optionally be added to the medium. When a microorganism transformed with an expression vector containing an inducible promoter is cultivated, an inducer may be added to the medium, if necessary. For example, when a microorganism transformed with an expression vector containing a Lac promoter is cultivated, isopropyl-β-thiogalactopyranoside (IPTG) may be added to the medium. When a microorganism transformed with an expression vector containing a trp promoter is cultivated, indoleacrylic acid (IAA) may be added to the medium.

After the cultivation, the modified hyperthermophilic DNA ligase, if produced in the host cell, is extracted by disruption of the cell. When the modified hyperthermophilic DNA ligase is produced in the exterior of the cell, the culture may be directly used as it is, or the modified hyperthermophilic DNA ligase may be isolated and purified from the culture, after removing the cell by centrifugation.

The isolation and purification of the modified hyperthermophilic DNA ligase may be carried out using any known procedure for use in isolation and purification of proteins, such as ammonium sulfate precipitation, SDS-PAGE, gel filtration, ion exchange chromatography, and affinity chromatography, singly or in any combination thereof.

The enzymatic activity of the modified hyperthermophilic DNA ligase according to the present invention can be determined by detecting ligation through fluorescence according typically to the method described in Examples below. Alternatively, the expression of the modified hyperthermophilic DNA ligase can be detected by preparing an antibody which binds specifically with the target modified hyperthermophilic DNA ligase and carrying out western blotting using the antibody.

3. LCR and Kit Therefore Using Modified Heat-Resistant Ligase

According to still other embodiments of the present invention, there are provided a method of carrying out a ligase chain reaction (LCR) using the modified hyperthermophilic DNA ligase, and a kit for LCR which contains the modified hyperthermophilic DNA ligase. As is described above, the modified hyperthermophilic DNA ligase maintains high enzymatic activity even at high temperatures and demonstrates outstanding performance in LCR requiring a temperature-cycling reaction. Specifically, LCR can be carried out more specifically and more rapidly and gene amplification and detection of point mutations can be efficiently carried out by using the modified hyperthermophilic DNA ligase which excels in thermal stability as well as in DNA binding ability and reactivity.

The kit for LCR according to the present invention essentially contains the modified hyperthermophilic DNA ligase according to the present invention. The kit may further contain any of reagents and devices which are generally required for LCR, such as an instruction manual, a surfactant, deoxynucleoside triphosphates (dNTPs; nucleotides), primers (nucleotides), a pH buffer, a magnesium solution, and cofactors such as other peptides and proteins.

The present invention will be illustrated in further detail with reference to specific embodiments below. It should be noted, however, the following embodiments are illustrated only by way of example and are never construed to limit the scope of the present invention.

First Embodiment

Preparation of C-Terminal Helix-Mutated Ligase
(1) Preparation of Genomic DNA of *Pyrococcus furiosus*

*Pyrococcus furiosus* DSM3638 was obtained from Deutsche Sammlung von Mikroorganismen und Zelkulturen GmbH and cultivated according to the method described in a document (Nucleic Acids Research, 21, 259-265 (1993)). About 1.2 g of cells was collected from the culture of 500 ml. This was suspended in 10 ml of Buffer L (10 mM Tris-HCl (pH 8.0), 1 mM EDTA, and 100 mM NaCl) and combined with 1 ml of 10% SDS. After stirring, 50 ml of proteinase K (20 mg/ml) was added, followed by standing at 55° C. for 60 minutes. The reaction mixture was sequentially subjected to extraction with phenol, extraction with phenol/chloroform mixture, and extraction with chloroform, followed by ethanol addition to insolubilize DNA. The DNA was recovered, dissolved in 1 ml of TE solution (10 mM Tris-HCl (pH 8.0) and 1 mM EDTA) and combined with 0.75 mg of RNase A, followed by a reaction at 37° C. for 60 minutes. The reaction mixture was subjected again to extraction with phenol, extraction with phenol/chloroform mixture, and extraction with chloroform, followed by precipitation from ethanol to recover DNA. Thus, 0.75 mg of DNA was obtained.

(2) Cloning of lig Gene

Primers were designed for amplification of a region expected to be the lig gene based on the genomic DNA of *Pyrococcus furiosus* through PCR. As primers for first PCR, 5'-CTAGTGGATCTGATGCGTTATCTGG-3' (SEQ ID NO: 9) and 5'-TCGGGACTATTGTTAGACCTTAGC-3' (SEQ ID NO: 10) were prepared. As primers for second PCR, 5'-GGCCATGGGTTATCTGGAGCTTGCTCAAC-3 (SEQ ID NO: 11) and 5'-GCGGATCCTTAGCTTTCCACTTTTCTTTCATC-3' (SEQ ID NO: 12) were prepared so as to anneal to the inside of the first primers, respectively. A NcoI-recognition sequence corresponding to ATG expected to be a translation initiation codon of the lig gene was integrated in forward primers. A BamHI-recognition sequence was introduced immediately downstream from the stop codon in reverse primers. The target gene was amplified by PCR using PyroBEST DNA polymerase (TAKARA BIO INC.). The PCR condition was 30 cycles of denaturation at 95° C., annealing at 55° C., and elongation at 72° C. Using the product of first PCR as a template, a second PCR was conducted under the same condition as above, and the product thereof was integrated into pGEM-T Easy vector (Promega Corporation), and the nucleotide sequence of the inserted fragment region was identified using a DNA sequencer (Beckman Coulter, Inc.). The lig gene was then cut out from the pGEM-T Easy vector through cleavage with NcoI-BamHI, inserted into pET21d vector (EMD Biosciences, Inc.), and thereby yielded a plasmid pET21d-lig. The NcoI sequence was introduced into the initiation codon site for constructing this expression system, whereby the second codon agg of SEQ ID NO: 1 was changed to ggt, and the second amino acid of the resulting translation product was changed from Arg to Gly (SEQ ID NOS: 3 and 4).

Mutagenesis was introduced according to site-directed mutagenesis using the plasmid pET21d-lig as a template in the following manner, so as to prepare a variant (Dala) in which all the aspartic acid residue at position 540, the glutamine residue at position 547, the lysine residue at position 554, and the lysine residue at position 558 are substituted by alanine residues. Using a set of primers for preparing a variant (K558A) with the lysine residue at position 558 being substituted by alanine and PyroBEST DNA polymerase (TAKARA BIO INC.), the target gene was amplified through PCR to yield a K558A plasmid. The set of primers used herein were 5'-GAAAAGATGAAAGGAGCAGTGGAAAGCTAA-3' (SEQ ID NO: 13) and 5'-TTAGCTTTCCACTGCTCCTTTCATCTTTTC-3' (SEQ ID NO: 14). The PCR condition was 20 cycles of denaturation at 95° C., annealing at 55° C., and elongation at 72° C. The target gene was further amplified through PCR by the above procedure, except for using the K558A plasmid as a template and a set of primers for preparing a variant (K554A/K558A) further with the lysine residue at position 554 being substituted by alanine. Thus, a K554A/K558A plasmid was obtained. The set of primers used herein were 5'-TACGAGTTGCAAGAAGCGATGAAAGGAGCA-3' (SEQ ID NO: 15) and 5'-TGCTCCTTTCATCGCTTCTTGCAACTCGTA-3' (SEQ ID NO: 16). Next, the target gene was further amplified through PCR by the above procedure, except for using the K554A/K558A plasmid as a template and a set of primers for preparing a variant (Q547A/K554A/K558A) further with the glutamine residue at position 547 being substituted by alanine. Thus, a Q547A/K554A/K558A plasmid was obtained. The set of primers used herein were 5'-ATAGAGAGAATCGCAGCACTTTACGAGTTG-3' (SEQ ID NO: 17) and 5'-CAACTCGTAAAGTGCTGCGATTCTCTCTAT-3' (SEQ ID NO: 18). The above PCR procedure was repeated, except for using the Q547A/K554A/K558A plasmid as a template and a set of primers for preparing a variant (Dala) with the aspartic acid residue at position 540 being substituted by alanine. The set of primers used herein were 5'-GGACCA-GAAGATGCAGCTACAATAGAGAGA-3' (SEQ ID NO: 19) and 5'-TCTCTCTATTGTAGCTGCATCTTCTGGTCC-3' (SEQ ID NO: 20). Thus, the final target Dala plasmid (pET21d-ligDala) was obtained.

Next, mutagenesis was introduced according to site-directed mutagenesis in the following manner, so as to prepare a variant (DΔ12) with the aspartic acid residue at position 540 and the glutamine residue at position 547 being substituted by alanine and with twelve amino acid residues from the C terminus being deleted. Specifically, site-directed mutagenesis was conducted by the above procedure, except for using the Dala plasmid as a template and a set of primers for preparing DΔ12 to insert a stop codon at position 12 residue from the C terminus. The set of primers used herein were 5'-ATCG-CACAACTTTACTAGTTGCAAGAAGCG-3' (SEQ ID NO: 21) and 5'-CGCTTCTTGCAACTAGTAAAGTTGTGC-GAT-3' (SEQ ID NO: 22). Thus, a DΔ12 plasmid (pET21d-ligDΔ12) was obtained.

(3) Construction of System for Expressing Large Amounts of *Pyrococcus Furiosus*-Derived Wild-Type Ligase and C-Terminal Helix-Modified Ligases (Dala, DΔ12) and Purification Thereof Hereinafter the construction of a system for expressing a large amount of the untreated (wild-type) ligase and purification thereof will be illustrated. This procedure could be adopted also to the C-terminal helix-modified ligases (Dala, DΔ12), except for using pET21d-ligDala and pET21d-ligDΔ12, respectively, as a first plasmid. These C-terminal helix-modified ligases could also be expressed and produced in large amounts.

BL21-CodonPlus-RIL competent cells (STRATAGENE) were transformed with the plasmid pET21d-lig, followed by cultivation at 37° C. in a Luria-Bertani medium containing 100 μg/mL ampicillin and 20 μg/mL chloramphenicol. When the turbidity of the culture in terms of absorbance at 660 nm reached 0.6, isopropyl-β-D-thiogalactopyranoside was added to a final concentration of 1 mM to thereby induce expression of protein. The cultivation was continued for further 6 hours, and cells were collected through centrifugal separation. The cells were suspended in Tris-HCl buffer (pH 8), subjected to disruption by the application of ultrasound, and to centrifugation separation. The supernatant was heated at 80° C. for 20 minutes, followed by centrifugal separation. Polyethyleneimine was added to the supernatant to a final concentration of 0.15% (w/v), from which nucleic acid components were removed by centrifugal separation. The resulting solution was combined with ammonium sulfate to 80% saturation, from which precipitates were collected by centrifugal separation.

The precipitates were dissolved in Tris-HCl buffer (pH 8), subjected to separation by affinity chromatography (HiTrap Heparin, 5 ml; GE Healthcare (formerly Amersham-Pharmacia Biotech)), and fractions eluted at NaCl concentrations of 0.4-0.5 M were collected. The fractions were further subjected to separation through anion exchange chromatography (HiTrap Q, 5 ml; GE Healthcare (formerly Amersham-Pharmacia Biotech)), and flow-through fractions were collected. The collected fractions as a solution were concentrated, subjected to separation through a gel filtration column (Superdex 200 HiLoad 26/60, GE Healthcare (formerly Amersham-Pharmacia Biotech)) at a flow rate of 1 ml/minute, and a main peak eluted at a retention time of about 100 minutes was collected. This solution was electrophoresed to find that the obtained protein has a purity of 99% or more and has a molecular weight lower than that of the native protein by the deleted residues at the C terminus. Thus, a modified DNA ligase according to the present invention could be easily obtained.

The nucleotide sequence of DNA encoding native (wild-type) DNA ligase derived from *Pyrococcus furiosus* is shown in SEQ ID NO: 1, and the amino acid sequence of the protein encoded thereby is shown in SEQ ID NO: 2. The C-terminal helix of the DNA ligase derived from *Pyrococcus furiosus* is composed of the amino acids 540 (Asp) to 561 (Ser) of SEQ ID NO: 2. The nucleotide sequence of the DNA encoding wild-type DNA ligase obtained according to the first embodiment is shown in SEQ ID NO: 3, and the amino acid sequence of the protein encoded thereby is shown in SEQ ID NO: 4. The nucleotide sequence of the DNA encoding the variant Dala obtained according to the first embodiment is shown in SEQ ID NO: 5, and the amino acid sequence of the protein encoded thereby is shown in SEQ ID NO: 6. The nucleotide sequence of the DNA encoding the variant DΔ12 obtained according to the first embodiment is shown in SEQ ID NO: 7, and the amino acid sequence of the protein encoded thereby is shown in SEQ ID NO: 8.

Second Embodiment

Comparison in Reactivity between C-Terminal Helix-Modified DNA Ligase Variants and Wild-Type Absorbances at 260 nm (OD260) of a template 60mer oligonucleotide, a 30mer oligonucleotide with phosphorylated 5' end, and a 20mer oligonucleotide with phosphor TFT-labeled 5' end were measured with a spectrophotometer (GeneSpeckIII, Hitachi High-Tech Manufacturing & Service Co., Ltd, (formerly Hitachinaka Instruments Co.)) to determine their concentrations. The concentrations of these oligonucleotides were adjusted to 0.5 mM, and each 5 μl of them were mixed to yield an oligonucleotide mixture. The nucleotide sequences of the oligonucleotides are 60mer: aaacgggccg gtcaacaatc ctctggagtc gacctgtagg aatgcaagct tggcgtcacg (SEQ ID NO: 23), 30mer: aggtcgactc cagaggattg ttgaccggcc (SEQ ID NO: 24), and 20mer: cgccaagctt gcattc-ctac (SEQ ID NO: 25). Next, the prepared oligonucleotide mixture was denatured at 95° C. for 5 minutes and annealed by decreasing the temperature from 94° C. to 2° C. at a rate of 1° C. per 5 minutes to thereby hybridize the three oligonucleotides. Using the annealing product as a template, ligation was conducted. The ligation product was electrophoresed on a 15% acrylamide/8 M urea gel. After electrophoresis, TET fluorescence intensities of bands at positions corresponding to 50mer as a ligation product and to the 20mer TET-labeled oligonucleotide were measured with the FluorImager 595 (GE Healthcare) and the image analyzing software ImageQuant (GE Healthcare (formerly Molecular Dynamics, Inc.)). The ratio of fluorescence intensity of the 50mer to the total of fluorescence intensities corresponding to the 50mer and the 20mer was defined as a ligation efficiency. Ligases were compared in ligation efficiency under the after-mentioned condition.

The prepared two variant DNA ligases were compared in ligation efficiency with the wild-type DNA ligase (N=2). FIG. 1 shows normalized ratios of ligation of the two variant DNA ligases relative to the ligation efficiency of the wild-type DNA ligase reacted at temperatures ranging from 20° C. to 90° C. The normalized ratios of ligation are ligation efficiencies of the variant DNA ligases with the average of ligation efficiencies of the wild-type DNA ligase at different reaction temperatures being 1. In FIG. 1, the plots indicated by the symbols of solid circle, solid rhombus, and solid square show the data of the wild-type, Dala, and DΔ12 DNA ligases, respectively.

The data demonstrate that the variant Dala shows higher ligation efficiencies at a low temperature (30° C.) and a high temperature (80° C.) and the variant DΔ12 shows higher ligation efficiencies at low temperatures (20° C. and 30° C.) and a high temperature (80° C.) than that of the wild-type DNA ligase.

Third Embodiment

Thermal Stability of Variant DNA Ligases

The DNA ligases including the native and variants used in the second embodiment were subjected to a heat treatment at 85° C. for 20 minutes at early stages of purification, to denature non-heat-resistant proteins and to make subsequent purification operations simple and easy. The variants show excellent thermal stability in the heat treatment.

According to the present invention, there are provided modified hyperthermophilic DNA ligases having high DNA binding ability and reactivity. The modified hyperthermophilic DNA ligases are useful for LCR and other nucleotide amplification techniques and genetic engineering techniques which require reactions at high temperatures. Accordingly, the present invention is applicable to the fields of biochemical researches, research reagents, diagnostic reagents, and pharmaceuticals.

Sequence Listing Free Text

SEQ ID NO: 1: DNA ligase derived from *Pyrococcus furiosus* (wild-type)
SEQ ID NO: 2: DNA ligase derived from *Pyrococcus furiosus* (wild-type)
SEQ ID NO: 3: DNA ligase derived from *Pyrococcus furiosus* (wild-type) obtained according to the first embodiment
SEQ ID NO: 4: DNA ligase derived from *Pyrococcus furiosus* (wild-type) obtained according to the first embodiment
SEQ ID NO: 5: DNA ligase derived from *Pyrococcus furiosus* (variant; Dala)
SEQ ID NO: 6: DNA ligase derived from *Pyrococcus furiosus* (variant; Dala)
SEQ ID NO: 7: DNA ligase derived from *Pyrococcus furiosus* (variant; DΔ12)
SEQ ID NO: 8: DNA ligase derived from *Pyrococcus furiosus* (variant; DΔ12)
SEQ ID NO: 9: primer for first PCR of DNA ligase derived from *Pyrococcus furiosus* (wild-type)
SEQ ID NO: 10: primer for first PCR of DNA ligase derived from *Pyrococcus furiosus* (wild-type)
SEQ ID NO: 11: primer for second PCR of DNA ligase derived from *Pyrococcus furiosus* (wild-type)
SEQ ID NO: 12: primer for second PCR of DNA ligase derived from *Pyrococcus furiosus* (wild-type)
SEQ ID NO: 13: primer for amplification of DNA ligase derived from *Pyrococcus furiosus* (variant; K558A)
SEQ ID NO: 14: primer for amplification of DNA ligase derived from *Pyrococcus furiosus* (variant; K558A)
SEQ ID NO: 15: primer for amplification of DNA ligase derived from *Pyrococcus furiosus* (variant; K554A/K558A)
SEQ ID NO: 16: primer for amplification of DNA ligase derived from *Pyrococcus furiosus* (variant; K554A/K558A)
SEQ ID NO: 17: primer for amplification of DNA ligase derived from *Pyrococcus furiosus* (variant; Q547A/K554A/K558A)
SEQ ID NO: 18: primer for amplification of DNA ligase derived from *Pyrococcus furiosus* (variant; Q547A/K554A/K558A)
SEQ ID NO: 19: primer for amplification of DNA ligase derived from *Pyrococcus furiosus* (variant; Dala)
SEQ ID NO: 20: primer for amplification of DNA ligase derived from *Pyrococcus furiosus* (variant; Dala)
SEQ ID NO: 21: primer for amplification of DNA ligase derived from *Pyrococcus furiosus* (variant; DΔ12)
SEQ ID NO: 22: primer for amplification of DNA ligase derived from *Pyrococcus furiosus* (variant; DΔ12)
SEQ ID NO: 23: 60mer substrate for wild-type DNA ligase derived from *Pyrococcus furiosus* and variants thereof
SEQ ID NO: 24: 30mer substrate for wild-type DNA ligase derived from *Pyrococcus furiosus* and variants thereof
SEQ ID NO: 25: 20mer substrate for wild-type DNA ligase derived from *Pyrococcus furiosus* and variants thereof.

What is claimed is:

1. A hyperthermophilic DNA ligase comprising the amino acid sequence of a heat-resistant DNA ligase, except with at least two of four amino acid residues each being substituted by one selected from the group consisting of alanine, threonine, and serine residues,
   wherein the four amino acid residues are residues of charged amino acids in a C-terminal helix region of the heat-resistant DNA ligase,
   wherein the heat-resistant DNA ligase is derived from *Pyrococcus furiosus* and comprises SEQ ID NO:2 and the four amino acid residues correspond to the aspartic acid residue at position 540, the glutamine residue at position 547, the lysine residue at position 554, and the lysine residue at position 558 of the amino acid sequence of SEQ ID NO: 2.

2. The hyperthermophilic DNA ligase according to claim 1, wherein all the four amino acid residues corresponding to the aspartic acid residue at position 540, the glutamine residue at position 547, the lysine residue at position 554, and the lysine residue at position 558 of the amino acid sequence encoded by SEQ ID NO: 1 are substituted.

3. The hyperthermophilic DNA ligase according to claim 1, wherein the substitutions are substitutions by alanine residues.

4. A hyperthermophilic DNA ligase comprising the amino acid sequence of a heat-resistant DNA ligase, except with at least two of four amino acid residues each being substituted by one selected from the group consisting of alanine, threonine, and serine residues,
   wherein the four amino acid residues are residues of charged amino acids in a C-terminal helix region of the heat-resistant DNA ligase,
   wherein the heat-resistant DNA ligase is derived from *Pyrococcus furiosus* and comprises SEQ ID NO: 2 and the four amino acid residues correspond to the aspartic acid residue at position 540, the glutamine residue at position 547, the lysine residue at position 554, and the lysine residue at position 558 of the amino acid sequence of SEQ ID NO: 2 and wherein the modified hyperthermophilic DNA ligase further comprises deletion of four to twelve amino acid residues from the C terminus in the C-terminal helix region.

5. A kit for LCR, comprising the hyperthermophilic DNA ligase of claim 1.

* * * * *

```
SEQUENCE LISTING

<160> NUMBER OF SEQ ID NOS: 35

<210> SEQ ID NO 1
<211> LENGTH: 1683
<212> TYPE: DNA
<213> ORGANISM: Pyrococcus furiosus

<400> SEQUENCE: 1
atgaggtatc tagagcttgc tcaactttat caaaagttag aaaagacaac tatgaaactt      60
ataaagacta gacttgtcgc cgacttcctg aaaaaagtac cagatgatca tctggagttc     120
attccctatc taattcttgg agaagttttt ccagagtggg atgaaaggga gctgggtgtg     180
ggagaaaagc tgttaattaa agctgtagca atggccactg gaattgacgc aaaagaaatc     240
gaagagtctg taaaagatac tggagacctt ggagagagca tagccttagc tgtaaagaaa     300
aagaagcaga agagcttctt ctctcagccc ctcacaataa gagggtata tcaaaccctt      360 gtaaaggttg cagaaacaac gggggaggga agccaagata aaaagtaaa gtatctagct      420 gatttgttca tggacgcaga acctttagaa gctaagtatc ttgctcgtac aatcttagga     480
```

```
acaatgagaa caggagttgc agaaggattg cttagagatg caatagcaat ggcattccac    540
gtaaaggtag agcttgttga gagagcttac atgctaacga gtgatttcgg atatgtagct    600
aaaatagcaa agcttgaagg aaatgaaggg ctagcaaaag ttcaagttca actcggaaag    660
ccaataaagc caatgcttgc ccagcaagct gctagcataa gagatgcact tctcgagatg    720
ggtggagagg cagagttcga gattaaatac gatggagcaa gggtgcaggt gcacaaggat    780
ggctcaaaaa ttatagtcta ttctagaaga ctggagaacg tcaccagagc gattccagaa    840
attgttgagg ctctaaaaga ggcaataata cctgaaaagg caatagtgga aggagaactt    900
gtggcaattg agaaaacgg aagaccattg cccttccaat atgtgcttag aaggtttagg     960
agaaagcata acatagaaga aatgatggaa aagatacctc tcgagctcaa cttattcgac   1020
gttctctacg tagatggaca aagcttgatt gacactaagt tcattgatag aagaagaaca   1080
cttgaagaaa taataaagca gaatgaaaag ataaaggtag cagaaaacct aataacaaag   1140
aaagtcgagg aagcagaggc attttacaag agagcactcg aaatggggca cgagggattg   1200
atggccaaga ggttagatgc agtctacgaa ccaggtaaca gaggaaagaa gtggttgaag   1260
ataaagccca aatggagaa cttagattta gtaatcatag gagcagaatg gggagaggga   1320
agaagagccc atctctttgg ttcattcatc ctgggagcat atgatccaga aacaggagaa   1380
ttcctagagg taggaaaagt gggaagtgga ttcacagatg atgacttagt tgagtttacg   1440
aagatgctaa agcccttat tataaaagag gaaggaaaga gagtctggct ccagcccaaa   1500
gttgttattg aagtgacata tcaagaaatt cagaagagtc caaaatacag aagtggattt   1560
gcattaaggt tcccaaggtt cgttgcactt agagatgata aaggaccaga agatgcagat   1620
acaatagaga gaatcgcaca actttacgag ttgcaagaaa agatgaaagg aaaagtggaa   1680
agc                                                                 1683
```

<210> SEQ ID NO 2
<211> LENGTH: 561
<212> TYPE: PRT
<213> ORGANISM: Pyrococcus furiosus

<400> SEQUENCE: 2

```
Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Glu Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160
```

-continued

```
Thr Met Arg Thr Gly Val Ala Glu Gly Leu Leu Arg Asp Ala Ile Ala
            165                 170                 175

Met Ala Phe His Val Lys Val Glu Leu Val Glu Arg Ala Tyr Met Leu
        180                 185                 190

Thr Ser Asp Phe Gly Tyr Val Ala Lys Ile Ala Lys Leu Glu Gly Asn
    195                 200                 205

Glu Gly Leu Ala Lys Val Gln Val Gln Leu Gly Lys Pro Ile Lys Pro
210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
        275                 280                 285

Ile Ile Pro Glu Lys Ala Ile Val Glu Gly Glu Leu Val Ala Ile Gly
    290                 295                 300

Glu Asn Gly Arg Pro Leu Pro Phe Gln Tyr Val Leu Arg Arg Phe Arg
305                 310                 315                 320

Arg Ser His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Arg Thr Leu Glu Glu Ile Ile Lys Gln Asn
        355                 360                 365

Glu Lys Ile Lys Val Ala Glu Asn Leu Ile Thr Lys Lys Val Glu Glu
    370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
    450                 455                 460

Gly Lys Val Gly Ser Gly Phe Thr Asp Asp Asp Leu Val Glu Phe Thr
465                 470                 475                 480

Lys Met Leu Lys Pro Leu Ile Ile Lys Glu Glu Gly Lys Arg Val Trp
                485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
        515                 520                 525

Ala Leu Arg Asp Asp Lys Gly Pro Glu Asp Ala Asp Thr Ile Glu Arg
    530                 535                 540

Ile Ala Gln Leu Tyr Glu Leu Gln Glu Lys Met Lys Gly Lys Val Glu
545                 550                 555                 560

Ser
```

<210> SEQ ID NO 3
<211> LENGTH: 1683

```
<212> TYPE: DNA
<213> ORGANISM: Pyrococcus furiosus

<400> SEQUENCE: 3
atgaggtatc tagagcttgc tcaactttat caaaagttag aaaagacaac tatgaaactt      60
ataaagacta gacttgtcgc cgacttcctg aaaaaagtac cagatgatca tctggagttc     120
attccctatc taattcttgg agaagttttt ccagagtggg atgaaaggga gctgggtgtg     180
ggagaaaagc tgttaattaa agctgtagca atggccactg gaattgacgc aaaagaaatc     240
gaagagtctg taaagatac tggagacctt ggagagagca tagccttagc tgtaaagaaa      300
aagaagcaga agagcttctt ctctcagccc ctcacaataa gagggtata tcaaacccctt     360
gtaaaggttg cagaaacaac gggggaggga agccaagata aaaagtaaa gtatctagct      420
gatttgttca tggacgcaga acctttagaa gctaagtatc ttgctcgtac aatcttagga     480
acaatgagaa caggagttgc agaaggattg cttagagatg caatagcaat ggcattccac     540
gtaaaggtag agcttgttga gagagcttac atgctaacga gtgatttcgg atatgtagct     600
aaaatagcaa gcttgaagg aaatgaaggg ctagcaaaag ttcaagttca actcggaaag      660
ccaataaagc caatgcttgc ccagcaagct gctagcataa gagatgcact tctcgagatg     720
ggtggagagg cagagttcga gattaaatac gatggagcaa gggtgcaggt gcacaaggat     780
ggctcaaaaa ttatagtcta ttctagaaga ctggagaacg tcaccagagc gattccagaa     840
attgttgagg ctctaaaaga ggcaataata cctgaaaagg caatagtgga aggagaactt     900
gtggcaattg agaaaacgg aagaccattg cccttccaat atgtgcttag aaggtttagg      960
agaaagcata acatagaaga aatgatggaa aagatacctc tcgagctcaa cttattcgac    1020
gttctctacg tagatggaca aagcttgatt gacactaagt tcattgatag aagaagaaca    1080
cttgaagaaa taataaagca gaatgaaaag ataaggtag cagaaaaccct aataacaaag     1140
aaagtcgagg aagcagaggc attttacaag agagcactcg aaatggggca cgagggattg    1200
atggccaaga ggttagatgc agtctacgaa ccaggtaaca gaggaaagaa gtggttgaag    1260
ataaagccca caatggagaa cttagattta gtaatcatag gagcagaatg gggagaggga    1320
agaagagccc atctctttgg ttcattcatc ctgggagcat atgatccaga acaggagaa     1380
ttcctagagg taggaaaagt gggaagtgga ttcacagatg atgacttagt tgagtttacg    1440
aagatgctaa agcccttat tataaagag gaaggaaaga gagctctggct ccagcccaaa      1500
gttgttattg aagtgacata tcaagaaatt cagaagagtc caaaatacag aagtggattt    1560
gcattaaggt tcccaaggtt cgttgcactt agagatgata aaggaccaga gatgcagat     1620
acaatagaga gaatcgcaca actttacgag ttgcaagaaa gatgaaaagg aaaagtggaa    1680
agc                                                                  1683
```

<210> SEQ ID NO 4
<211> LENGTH: 561
<212> TYPE: PRT
<213> ORGANISM: Pyrococcus furiosus

<400> SEQUENCE: 4

Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
                20                  25                  30

Val Pro Asp Asp His Leu Glu Phe Ile Pro Tyr Leu Ile Leu Gly Glu
            35                  40                  45

```
Val Phe Pro Glu Trp Asp Glu Arg Glu Leu Gly Val Gly Glu Lys Leu
     50                  55                  60

Leu Ile Lys Ala Val Ala Met Ala Thr Gly Ile Asp Ala Lys Glu Ile
 65                  70                  75                  80

Glu Glu Ser Val Lys Asp Thr Gly Asp Leu Gly Glu Ser Ile Ala Leu
                 85                  90                  95

Ala Val Lys Lys Lys Gln Lys Ser Phe Phe Ser Gln Pro Leu Thr
                100                 105                 110

Ile Lys Arg Val Tyr Gln Thr Leu Val Lys Val Ala Glu Thr Thr Gly
            115                 120                 125

Glu Gly Ser Gln Asp Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
                260                 265                 270

Asn Val Thr Arg Ala Ile Pro Glu Ile Val Glu Ala Leu Lys Glu Ala
            275                 280                 285

Ile Ile Pro Glu Lys Ala Ile Val Glu Gly Glu Leu Val Ala Ile Gly
        290                 295                 300

Glu Asn Gly Arg Pro Leu Pro Phe Gln Tyr Val Leu Arg Arg Phe Arg
305                 310                 315                 320

Arg Ser His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Thr Leu Glu Glu Ile Ile Lys Gln Asn
        355                 360                 365

Glu Lys Ile Lys Val Ala Glu Asn Leu Ile Thr Lys Lys Val Glu Glu
    370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
    450                 455                 460

Gly Lys Val Gly Ser Gly Phe Thr Asp Asp Leu Val Glu Phe Thr
465                 470                 475                 480
```

```
            Lys Met Leu Lys Pro Leu Ile Ile Lys Glu Glu Gly Lys Arg Val Trp
                            485                 490                 495

Leu Gln Pro Lys Val Val Ile Glu Val Thr Tyr Gln Glu Ile Gln Lys
                        500                 505                 510

Ser Pro Lys Tyr Arg Ser Gly Phe Ala Leu Arg Phe Pro Arg Phe Val
                        515                 520                 525

Ala Leu Arg Asp Asp Lys Gly Pro Glu Asp Ala Asp Thr Ile Glu Arg
                        530                 535                 540

Ile Ala Gln Leu Tyr Glu Leu Gln Glu Lys Met Lys Gly Lys Val Glu
            545                 550                 555                 560

Ser

<210> SEQ ID NO 5
            <211> LENGTH: 1683
            <212> TYPE: DNA
            <213> ORGANISM: Pyrococcus furiosus

<400> SEQUENCE: 5
atgaggtatc tagagcttgc tcaactttat caaaagttag aaaagacaac tatgaaactt       60
ataaagacta gacttgtcgc cgacttcctg aaaaaagtac cagatgatca tctggagttc      120
attccctatc taattcttgg agaagttttt ccagagtggg atgaaaggga gctgggtgtg      180
ggagaaaagc tgttaattaa agctgtagca atggccactg gaattgacgc aaaagaaatc      240
gaagagtctg taaagatac tggagacctt ggagagagca tagccttagc tgtaaagaaa      300
aagaagcaga gagcttcttc tctcagccct ctcacaataa gagggtata tcaaaccctt       360 gtaaaggttg cagaaacaac gggggaggga agccaagata aaaaagtaaa gtatctagct      420
gatttgttca tggacgcaga accttttagaa gctaagtatc ttgctcgtac aatcttagga      480
acaatgagaa caggagttgc agaaggattg cttagagatg caatagcaat ggcattccac      540
gtaaaggtag agcttgttga gagagcttac atgctaacga gtgatttcgg atatgtagct      600
aaaatagcaa agcttgaagg aaatgaaggg ctagcaaaag ttcaagttca actcggaaag      660
ccaataaagc caatgcttgc ccagcaagct gctagcataa gagatgcact tctcgagatg      720
ggtggagagg cagagttcga gattaaatac gatggagcaa gggtgcaggt gcacaaggat      780
ggctcaaaaa ttatagtcta ttctagaaga ctggagaacg tcaccagagc gattccagaa      840
attgttgagg ctctaaaaga ggcaataata cctgaaaagg caatagtgga aggagaactt      900
gtggcaattg agaaaacgg aagaccattg cccttccaat atgtgcttag aaggtttagg      960
agaaagcata acatagaaga aatgatggaa aagatacctc tcgagctcaa cttattcgac     1020
gttctctacg tagatggaca aagcttgatt gacactaagt tcattgatag aagaagaaca     1080
cttgaagaaa taataaagca gaatgaaaag ataaaggtag cagaaaacct aataacaaag     1140
aaagtcgagg aagcagaggc attttacaag agagcactcg aaatgggggca cgagggattg     1200 atggccaaga ggttagatgc agtctacgaa ccaggtaaca gaggaaagaa gtggttgaag     1260
ataaagccca atgcgagaa cttagattta gtaatcatag gagcagaatg gggagaggga     1320
agaagagccc atctctttgg ttcattcatc ctgggagcat atgatccaga aacaggagaa     1380
ttcctagagg taggaaaagt gggaagtgga ttcacagatg atgacttagt tgagtttacg     1440
aagatgctaa agcccttat tataaaagag gaaggaaaga gagtctggct ccagcccaaa     1500
gttgttattg aagtgacata tcaagaaatt cagaagagtc caaaatacag aagtggatt      1560 gcattaaggt tcccaaggtt cgttgcactt agagatgata aaggaccaga gatgcagct      1620
```

```
acaatagaga gaatcgcagc actttacgag ttgcaagaag cgatgaaagg agcagtggaa    1680
agc                                                                  1683
```

<210> SEQ ID NO 6
<211> LENGTH: 561
<212> TYPE: PRT
<213> ORGANISM: Pyrococcus furiosus

<400> SEQUENCE: 6

```
Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Glu Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
        275                 280                 285

Ile Ile Pro Glu Lys Ala Ile Val Gly Glu Leu Val Ala Ile Gly
    290                 295                 300

Glu Asn Gly Arg Pro Leu Pro Phe Gln Tyr Val Leu Arg Arg Phe Arg
305                 310                 315                 320

Arg Ser His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Arg Thr Leu Glu Glu Ile Ile Lys Gln Asn
        355                 360                 365
```

```
Glu Lys Ile Lys Val Ala Glu Asn Leu Ile Thr Lys Lys Val Glu Glu
    370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
    450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
                485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
        515                 520                 525

Ala Leu Arg Asp Asp Lys Gly Pro Glu Asp Ala Ala Thr Ile Glu Arg
    530                 535                 540

Ile Ala Ala Leu Tyr Glu Leu Gln Glu Ala Met Lys Gly Ala Val Glu
545                 550                 555                 560

Ser

<210> SEQ ID NO 7
<211> LENGTH: 1650
<212> TYPE: DNA
<213> ORGANISM: Pyrococcus furiosus

<400> SEQUENCE: 7
atgaggtatc tagagcttgc tcaactttat caaaagttag aaaagacaac tatgaaactt      60
ataaagacta gacttgtcgc cgacttcctg aaaaaagtac cagatgatca tctggagttc     120
attccctatc taattcttgg agaagttttt ccagagtggg atgaaaggga gctgggtgtg     180
ggagaaaagc tgttaattaa agctgtagca atggccactg gaattgacgc aaaagaaatc     240
gaagagtctg taaagatac tggagacctt ggagagagca tagccttagc tgtaaagaaa     300
aagaagcaga gagcttcttt ctctcagccc ctcacaataa gagggtata tcaaaccctt     360 gtaaggttg cagaaacaac gggggaggga agccaagata aaaagtaaa gtatctagct     420 gatttgttca tggacgcaga accttttagaa gctaagtatc ttgctcgtac aatcttagga     480
acaatgagaa caggagttgc agaaggattg cttagagatg caatagcaat ggcattccac     540
gtaaaggtag agcttgttga gagagcttac atgctaacga gtgatttcgg atatgtagct     600
aaaatagcaa agcttgaagg aaatgaaggg ctagcaaaag ttcaagttca actcggaaag     660
ccaataaagc caatgcttgc ccagcaagct gctagcataa gagatgcact tctcgagatg     720
ggtggagagg cagagttcga gattaaatac gatggagcaa gggtgcaggt gcacaaggat     780
ggctcaaaaa ttatagtcta ttctagaaga ctggagaacg tcaccagagc gattccagaa     840
attgttgagg ctctaaaaga ggcaataata cctgaaaagg caatagtgga aggagaactt     900
gtggcaattg gagaaaacgg aagaccattg cccttccaat atgtgcttag aaggtttagg     960
agaaagcata acatagaaga aatgatggaa agataccctc tcgagctcaa cttattcgac    1020
```

-continued

```
gttctctacg tagatggaca aagcttgatt gacactaagt tcattgatag aagaagaaca    1080
cttgaagaaa taataaagca gaatgaaaag ataaaggtag cagaaaacct aataacaaag    1140
aaagtcgagg aagcagaggc attttacaag agagcactcg aaatgggca cgagggattg     1200 atggccaaga ggttagatgc agtctacgaa ccaggtaaca gaggaaagaa gtggttgaag    1260
ataaagccca atggagaa cttagattta gtaatcatag gagcagaatg gggagaggga      1320
agaagagccc atctctttgg ttcattcatc ctgggagcat atgatccaga aacaggagaa    1380
ttcctagagg taggaaaagt gggaagtgga ttcacagatg atgacttagt tgagtttacg    1440
aagatgctaa agccccttat tataaaagag gaaggaaaga gagtctggct ccagcccaaa    1500
gttgttattg aagtgacata tcaagaaatt cagaagagtc caaaatacag aagtggattt    1560
gcattaaggt tcccaaggtt cgttgcactt agagatgata aaggaccaga agatgcagct    1620
acaatagaga gaatcgcagc actttactag                                     1650
```

<210> SEQ ID NO 8
<211> LENGTH: 549
<212> TYPE: PRT
<213> ORGANISM: Pyrococcus furiosus

<400> SEQUENCE: 8

```
Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Glu Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
```

```
                    260                 265                 270
Asn Val Thr Arg Ala Ile Pro Glu Ile Val Glu Ala Leu Lys Glu Ala
            275                 280                 285
Ile Ile Pro Glu Lys Ala Ile Val Glu Gly Glu Leu Val Ala Ile Gly
        290                 295                 300
Glu Asn Gly Arg Pro Leu Pro Phe Gln Tyr Val Leu Arg Arg Phe Arg
305                 310                 315                 320
Arg Ser His Asn Ile Glu Glu Met Met Glu Lys Ile Pro Leu Glu Leu
                325                 330                 335
Asn Leu Phe Asp Val Leu Tyr Val Asp Gly Gln Ser Leu Ile Asp Thr
            340                 345                 350
Lys Phe Ile Asp Arg Arg Thr Leu Glu Glu Ile Ile Lys Gln Asn
        355                 360                 365
Glu Lys Ile Lys Val Ala Glu Asn Leu Ile Thr Lys Lys Val Glu Glu
        370                 375                 380
Ala Glu Ala Phe Tyr Lys Arg Ala Leu Glu Met Gly His Glu Gly Leu
385                 390                 395                 400
Met Ala Lys Arg Leu Asp Ala Val Tyr Glu Pro Gly Asn Arg Gly Lys
                405                 410                 415
Lys Trp Leu Lys Ile Lys Pro Thr Met Glu Asn Leu Asp Leu Val Ile
            420                 425                 430
Ile Gly Ala Glu Trp Gly Glu Gly Arg Arg Ala His Leu Phe Gly Ser
            435                 440                 445
Phe Ile Leu Gly Ala Tyr Asp Pro Gly Thr Gly Glu Phe Leu Glu Val
        450                 455                 460
Gly Lys Val Gly Ser Gly Phe Thr Asp Asp Asp Leu Val Glu Phe Thr
465                 470                 475                 480
Lys Met Leu Lys Pro Leu Ile Ile Lys Glu Glu Gly Lys Arg Val Trp
                485                 490                 495
Leu Gln Pro Lys Val Val Ile Glu Val Thr Tyr Gln Glu Ile Gln Lys
            500                 505                 510
Ser Pro Lys Tyr Arg Ser Gly Phe Ala Leu Arg Phe Pro Arg Phe Val
        515                 520                 525
Ala Leu Arg Asp Asp Lys Gly Pro Glu Asp Ala Thr Ile Glu Arg
        530                 535                 540
Ile Ala Ala Leu Tyr
545

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctagtggatc tgatgcgtta tctgg                                          25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
```
tcgggactat tgttagacct tagc                                          24

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggccatgggt tatctggagc ttgctcaac                                     29

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcggatcctt agctttccac ttttctttca tc                                 32

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 gaaagatga aggagcagt ggaaagctaa                                      30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14 ttagcttttcc actgctcctt tcatcttttc                                   30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tacgagttgc aagaagcgat gaaaggagca                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgctcctttc atcgcttctt gcaactcgta                                    30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atagagagaa tcgcagcact ttacgagttg                                      30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caactcgtaa agtgctgcga ttctctctat                                      30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaccagaag atgcagctac aatagagaga                                      30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctctctatt gtagctgcat cttctggtcc                                      30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcgcacaac tttactagtt gcaagaagcg                                      30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgcttcttgc aactagtaaa gttgtgcgat                                      30

<210> SEQ ID NO 23

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaacgggccg gtcaacaatc ctctggagtc gacctgtagg aatgcaagct tggcgtcacg     60

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aggtcgactc cagaggattg ttgaccggcc                                      30

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgccaagctt gcattcctac                                                 20

<210> SEQ ID NO 26
<211> LENGTH: 88
<212> TYPE: PRT
<213> ORGANISM: Pyrobaculum aerophilum

<400> SEQUENCE: 26

His Arg His Pro Arg Val Val Ser Lys Met Glu Ala Asp Val Trp Phe
1               5                   10                  15

Val Pro Gln Val Val Ile Glu Val Ile Gly Ala Glu Ile Thr Leu Ser
            20                  25                  30

Pro Leu His Thr Cys Cys Leu Gly Ala Val Arg Pro Gly Val Gly Leu
        35                  40                  45

Ala Val Arg Phe Pro Arg Phe Thr Gly Arg Tyr Arg Ser Asp Lys Ser
    50                  55                  60

Pro Glu Gln Ala Thr Thr Val Ala Glu Met Leu Glu Leu Tyr Lys Arg
65                  70                  75                  80

Gln Lys Lys Val Val Gln Pro Glu
                85

<210> SEQ ID NO 27
<211> LENGTH: 92
<212> TYPE: PRT
<213> ORGANISM: Desufurolobus ambivalens

<400> SEQUENCE: 27

Thr Pro His Pro Arg Val Val Ser Thr Met Val Pro Asp Val Trp Leu
1               5                   10                  15

Thr Pro Ala Leu Val Ala Glu Ile Ile Gly Ala Glu Ile Thr Ile Ser
            20                  25                  30

Pro Leu His Thr Cys Cys Lys Asp Gln Tyr Ala Glu Gly Gly Leu Ser
        35                  40                  45
```

-continued

Ile Arg Phe Pro Arg Phe Ile Arg Trp Arg Pro Asp Lys Ser Pro Glu
        50                  55                  60

Asp Ala Thr Thr Asn Arg Glu Ile Leu Glu Met Tyr Lys Ser Gln Leu
65                  70                  75                  80

Lys Lys Ile Glu Glu Lys Pro Ser Asp Gln Ser Val
                85                  90

<210> SEQ ID NO 28
<211> LENGTH: 69
<212> TYPE: PRT
<213> ORGANISM: Archaeglobus fulgidus

<400> SEQUENCE: 28

Gln Gln Gly Lys Lys Val Glu Phe Ile Pro Lys Tyr Val Phe Glu Val
1               5                   10                  15

Ala Tyr Gln Glu Ile Gln Lys Ser Pro Lys Tyr Glu Ser Gly Tyr Ala
                20                  25                  30

Leu Arg Phe Pro Arg Phe Val Arg Leu Pro Asp Lys Asp Val Asp
            35                  40                  45

Glu Ala Asp Thr Ile Glu Arg Val Glu Asn Leu Tyr Lys Leu Gln Phe
        50                  55                  60

Glu Val Lys Arg Gln
65

<210> SEQ ID NO 29
<211> LENGTH: 69
<212> TYPE: PRT
<213> ORGANISM: Methanobacterium thermoautotrophicum

<400> SEQUENCE: 29

Arg Lys Gly Arg Lys Leu Leu Val Arg Pro Gly Ile Ile Leu Glu Val
1               5                   10                  15

Ala Tyr Ser Glu Ile Val Lys Ser Pro Glu Tyr Glu Ser Gly Tyr Ser
                20                  25                  30

Leu Arg Phe Pro Val Val Lys Arg Ile Arg Asp Asp Leu Cys Leu Asp
            35                  40                  45

Asp Val Asp Thr Val Gly Arg Ile Glu Ser Leu Phe Gln Ser Gly Gln
        50                  55                  60

Pro Asp Gln Pro Gly
65

<210> SEQ ID NO 30
<211> LENGTH: 67
<212> TYPE: PRT
<213> ORGANISM: Methanococcus jannaschii

<400> SEQUENCE: 30

Asp Leu Gly Glu Glu Val Glu Val Glu Pro Lys Ile Val Ile Glu Val
1               5                   10                  15

Ala Tyr Glu Glu Ile Gln Lys Ser Asp Lys Tyr Pro Cys Gly Tyr Ala
                20                  25                  30

Leu Arg Phe Pro Arg Val Val Arg Phe Arg Phe Asp Lys Gly Val Asn
            35                  40                  45

Glu Ile Asn Thr Ile Glu Asp Val Glu Arg Ile Tyr Glu Ile Gln Arg
        50                  55                  60

Gly Arg Lys
65

<210> SEQ ID NO 31

```
<211> LENGTH: 70
<212> TYPE: PRT
<213> ORGANISM: Thermococcus kodakaraensis

<400> SEQUENCE: 31

Gln Glu Gly Lys Phe Val Glu Ile Glu Pro Lys Phe Val Ile Glu Val
1               5                   10                  15

Thr Tyr Gln Glu Ile Gln Lys Ser Pro Lys Tyr Lys Ser Gly Phe Ala
            20                  25                  30

Leu Arg Phe Pro Arg Tyr Val Ala Leu Arg Glu Asp Lys Ser Pro Glu
        35                  40                  45

Glu Ala Asp Thr Ile Glu Arg Val Ala Glu Leu Tyr Glu Leu Gln Glu
    50                  55                  60

Arg Phe Lys Ala Lys Lys
65                  70

<210> SEQ ID NO 32
<211> LENGTH: 70
<212> TYPE: PRT
<213> ORGANISM: Pyrococcus abyssi

<400> SEQUENCE: 32

Glu Glu Gly Lys Arg Val Trp Ile Gln Pro Lys Val Val Ile Glu Val
1               5                   10                  15

Thr Tyr Gln Glu Ile Gln Lys Ser Pro Lys Tyr Arg Ser Gly Phe Ala
            20                  25                  30

Leu Arg Phe Pro Arg Tyr Val Ala Leu Arg Glu Asp Lys Gly Pro Glu
        35                  40                  45

Asp Ala Asp Thr Ile Glu Arg Ile Ala Gln Leu Tyr Glu Leu Gln Glu
    50                  55                  60

Arg Met Lys Gly Lys Val
65                  70

<210> SEQ ID NO 33
<211> LENGTH: 72
<212> TYPE: PRT
<213> ORGANISM: Pyrococcus furiosus

<400> SEQUENCE: 33

Glu Glu Gly Lys Arg Val Trp Leu Gln Pro Lys Val Val Ile Glu Val
1               5                   10                  15

Thr Tyr Gln Glu Ile Gln Lys Ser Pro Lys Tyr Arg Ser Gly Phe Ala
            20                  25                  30

Leu Arg Phe Pro Arg Phe Val Ala Leu Arg Asp Asp Lys Gly Pro Glu
        35                  40                  45

Asp Ala Asp Thr Ile Glu Arg Ile Ala Gln Leu Tyr Glu Leu Gln Glu
    50                  55                  60

Lys Met Lys Gly Lys Val Glu Ser
65                  70

<210> SEQ ID NO 34
<211> LENGTH: 101
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Orn

<400> SEQUENCE: 34

Ser Pro Arg Pro Tyr Val Arg Ile Asp Gly Ala Val Ile Pro Xaa His
```

-continued

```
                1               5                  10                   15

Trp Leu Asp Pro Ser Ala Val Trp Glu Val Lys Cys Ala Asp Leu Ser
            20                  25                  30

Leu Ser Pro Ile Tyr Pro Ala Ala Arg Gly Leu Val Asp Ser Asp Lys
            35                  40                  45

Gly Ile Ser Leu Arg Phe Pro Arg Phe Ile Arg Val Arg Glu Asp Lys
            50                  55                  60

Gln Pro Glu Gln Ala Thr Thr Ser Ala Gln Val Ala Cys Leu Tyr Arg
65                  70                  75                  80

Lys Gln Ser Gln Ile Gln Asn Gln Gln Gly Glu Asp Ser Gly Ser Asp
                85                  90                  95

Pro Glu Asp Thr Tyr
                100

<210> SEQ ID NO 35
<211> LENGTH: 85
<212> TYPE: PRT
<213> ORGANISM: Saccharomyces cerevisiae

<400> SEQUENCE: 35

Gly Pro Lys Ala Thr Phe Val Phe Asp Ser Ser Ala Glu Pro Asp Val
1               5                   10                  15

Trp Phe Glu Pro Thr Thr Leu Phe Glu Val Leu Thr Ala Asp Leu Ser
            20                  25                  30

Leu Ser Pro Ile Tyr Lys Ala Gly Ser Ala Thr Phe Asp Lys Gly Val
            35                  40                  45

Ser Leu Arg Phe Pro Arg Phe Leu Arg Ile Arg Glu Asp Lys Gly Val
            50                  55                  60

Glu Asp Ala Thr Ser Ser Asp Gln Ile Val Glu Leu Tyr Glu Asn Gln
65                  70                  75                  80

Ser His Met Gln Asn
                85
```